United States Patent
Xu et al.

(10) Patent No.: US 12,303,205 B2
(45) Date of Patent: *May 20, 2025

(54) TKA INTRAOPERATIVE PLANNING ADJUSTMENT METHOD, APPARATUS AND DEVICE FOR TKA

(71) Applicant: TINAVI MEDICAL TECHNOLOGIES CO., LTD, Beijing (CN)

(72) Inventors: Ziang Xu, Beijing (CN); Zhan Wang, Beijing (CN); Zongxiang Liu, Beijing (CN)

(73) Assignee: TINAVI MEDICAL TECHNOLOGIES CO., LTD, Beijing (CN)

( * ) Notice: Subject to any disclaimer, the term of this patent is extended or adjusted under 35 U.S.C. 154(b) by 1065 days.

This patent is subject to a terminal disclaimer.

(21) Appl. No.: 17/287,438

(22) PCT Filed: Nov. 16, 2020

(86) PCT No.: PCT/CN2020/129136
§ 371 (c)(1),
(2) Date: Apr. 21, 2021

(87) PCT Pub. No.: WO2021/147489
PCT Pub. Date: Jul. 29, 2021

(65) Prior Publication Data
US 2022/0175452 A1    Jun. 9, 2022

(30) Foreign Application Priority Data

Jan. 21, 2020 (CN) .......................... 202010072017.3

(51) Int. Cl.
*A61B 34/10* (2016.01)
*A61B 34/20* (2016.01)

(52) U.S. Cl.
CPC ........ *A61B 34/10* (2016.02); *A61B 2034/102* (2016.02); *A61B 2034/104* (2016.02); *A61B 2034/105* (2016.02); *A61B 2034/108* (2016.02); *A61B 2034/2055* (2016.02)

(58) Field of Classification Search
CPC .............. A61B 34/10; A61B 2034/102; A61B 2034/104; A61B 2034/105; A61B 2034/108; A61B 2034/2055; A61B 34/20
See application file for complete search history.

(56) References Cited

U.S. PATENT DOCUMENTS 7,708,741 B1    5/2010  Bonutti

FOREIGN PATENT DOCUMENTS

| CN | 101254103 A | 9/2008 | |
|---|---|---|---|
| CN | 101711127 A | 5/2010 | |
| CN | 107106239 A | 8/2017 | |
| CN | 109496143 A | 3/2019 | |
| CN | 111249002 A | 6/2020 | |
| CN | 111345895 A | 6/2020 | |
| WO | WO-2017204832 A1 * | 11/2017 | ......... A61B 17/3209 |

OTHER PUBLICATIONS

Dr. Bertrand Kaper et al. for Smith & Nephew [NAVIO7 TKA Gap Balancing Workflow, (Jul. 28, 2019), XP093134395, retrieved from the Internet: https://hmvw.youtube.com/watch?v=IqekXcps73s] (Year: 2019) 23 pages.*
International Search Report issued by the International Searching Authority for corresponding International Patent Application No. PCT/CN2020/129136, mailed on Feb. 19, 2021.

* cited by examiner

*Primary Examiner* — Lori A. Clow
*Assistant Examiner* — Vy Rossi
(74) *Attorney, Agent, or Firm* — MYERS WOLIN, LLC

(57) ABSTRACT

Provided are an intraoperative planning adjustment method, apparatus and device for TKA (Total Knee Arthroplasty) and a computer-readable medium. The method comprises: importing preoperative planning data; performing image registration on preoperative planning images and the surface contour of a knee joint of a surgical object; acquiring the dynamic spacing force line data of the knee joint at a continuous flexion-extension angle; visually displaying the dynamic spacing force line data graph; and adjusting prosthesis planning according to the visual display of the dynamic spacing force line data. By calculating information such as the joint gap and the force line angle of the lower limb at the continuous flexion-extension angle in the operation, the method provides a comprehensive adjustment information source in the operation for a surgeon, and therefore a better operation planning is obtained.

13 Claims, 6 Drawing Sheets

TKA INTRAOPERATIVE PLANNING ADJUSTMENT METHOD, APPARATUS AND DEVICE FOR TKA

CROSS REFERENCE TO RELATED APPLICATIONS

The present application is a U.S. National Phase of International Patent Application Serial No. PCT/CN2020/129136, filed on Nov. 16, 2020, which claims priority to Chinese Application 202010072017.3, filed on Jan. 21, 2020, the contents of each of which are incorporated by reference in their entirety for all purposes.

TECHNICAL FIELD

The present application relates to the technical filed of joint replacement and particularly relates to an intraoperative planning adjustment method, apparatus and electronic device for TKA (Total Knee Arthroplasty) and a computer-readable medium.

BACKGROUND

Total Knee Arthroplasty (TKA) is a new technology for the treatment of knee joint diseases. By replacing the joint surface of the knee joint with a prosthetic part, it can effectively eradicate severe knee joint pain and greatly improve the quality of life of surgical objects. Factors that affect the effect of joint replacement include accurate osteotomy in three-dimensional space, balance and stability of soft tissues such as ligaments, and the position and angle of prosthesis placement. The TKA has particularly strict requirements for these factors.

The application of a computer-aided system in TKA has greatly improved the accuracy of the operation, shortened the operation time, and reduced the additional damage to the surgical objects caused by the traditional surgical process. Generally, the computer-aided system in TKA includes preoperative planning and intraoperative planning. In preoperative planning, a 3D model of the skeletal anatomy of the surgical object is generally generated from the computer tomography (CT) or magnetic resonance imaging (MRI) image data set of the surgical object, the preoperative coordinate system is determined and the image is corrected. A set of 3D models of joint prosthesis is loaded into the system, surgeons are allowed to place the desired joint prosthesis model into the 3D model of the bone anatomy, adjust the position and direction of the joint prosthesis, and select a joint prosthesis with a suitable model size to realize the preoperative optimal cooperation of joint prosthesis and bones.

Preoperative planning is based on the 3D reconstruction model of the surgical object, which has certain errors and can only reflect the static information of the bones. Therefore, it is necessary to adjust the preoperative planning according to the lower limb force line of the surgical object and the dynamic position information of the lower limb dining the operation to achieve a better surgical effect. The existing intraoperative planning adjustment method can provide a surgeon with information on the force line and gap of the lower limb at a lower limb flexion-extension angle of 0° and 90°. The surgeon can adjust the planning position of the prosthesis during the operation and optimize the osteotomy plan based on the above information. However, the range of flexion-extension angles that the knee joint can reach is from −10° to 130°. To improve the postoperative effect of surgery and achieve long-term use of the prosthesis, it is required to ensure accurate alignment of force line and soft tissue balance, and it is far from enough to adjust the intraoperative planning based on the information at the flexion-extension angle of 0° and 90°.

SUMMARY OF THE INVENTION

In order to solve the problem of a single source of information for intraoperative planning adjustment in the prior art, the present application provides an intraoperative planning adjustment method for TKA, comprising:
  importing preoperative planning data;
  performing image registration of preoperative planning images with the surface contour of a knee joint of a surgical object;
  acquiring the dynamic spacing force line data of the knee joint at a continuous flexion-extension angle;
  visually displaying the dynamic spacing force line data graph; and
  adjusting prosthesis planning according to the visual display of the dynamic spacing force line data.

According to some embodiments of the present application, the preoperative planning data comprises joint prosthesis data and/or a preliminary osteotomy plan.

According to some embodiments of the present application, the acquiring the dynamic spacing force line data of the knee joint at a continuous flexion-extension angle comprises:
  acquiring the motion trajectory information of the knee joint during the continuous flexion-extension of a lower limb; and
  calculating the gap and force line angle of the lower limb at a continuous flexion-extension angle.

According to some embodiments of the present application, the acquiring the motion trajectory information of the knee joint during the continuous flexion-extension of a lower limb comprises:
  setting tracers on the femur and tibia of the knee joint; and
  during the continuous flexion-extension of the lower limb, continuously tracking the tracers by an optical camera, and acquiring and recording the motion trajectory information of the knee joint.

According to some embodiments of the present application, the gap and force line angle comprises:
  a first gap, being a minimum gap between the outer surface of the medial femoral condyle of the prosthesis and the tibial osteotomy plane;
  a second gap, being a minimum gap between the outer surface of the lateral femoral condyle of the prosthesis and the tibial osteotomy plane; and
  a force line angle, being an angle between a femoral mechanical axis and a tibial mechanical axis.

According to some embodiments of the present application, calculating the gap comprises:
  calculating the lowest point of the curved surface of the outer surface of the prosthetic femur on the neutral vertical axis of the human body; and
  calculating the distance from the lowest point to the tibial osteotomy plane.

According to some embodiments of the present application, calculating the gap comprises:
  obtaining a first projection by projecting the curved surface of the outer surface of the prosthetic femur on the neutral coronal plane of the human body;

obtaining a second projection by projecting the tibia osteotomy plane on the neutral coronal plane of the human body; and calculating the minimum distance from the first projection to the second projection.

According to some embodiments of the present application, calculating the force line angle comprises:

projecting the femoral mechanical axis on the neutral coronal plane of the human body to obtain a femoral projection axis;

projecting the tibial force line on the neutral coronal plane of the human body to obtain the tibial projection axis; and calculating the angle between the femoral projection axis and the tibial projection axis.

According to some embodiments of the present application, the dynamic spacing force line data graph comprises:

a first gap curve, a continuous curve drawn by taking the flexion-extension angle of the lower limb as an ordinate and the first gap as a first abscissa;

a second gap curve, a continuous curve drawn by taking the flexion-extension angle of the lower limb as an ordinate and the second gap as a first abscissa; and a force line angle change curve, drawn by taking the flexion-extension angle of the lower limb as an ordinate and the force line angle as an abscissa.

According to some embodiments of the present application, the midpoint of the first abscissa is the origin and extends positively to the left and right sides, and the first gap curve and the second gap curve are respectively arranged on both sides of the midpoint of the first abscissa.

According to some embodiments of the present application, the adjusting prosthesis planning comprises:

receiving position adjustment information of the prosthesis interacted by the surgeon; and recalculating the gap and force line and refreshing the dynamic spacing force line data graph.

According to some embodiments of the present application, the prosthesis position information comprises at least one of varus/valgus angle, external/internal rotation angle, anterior/posterior slope angle, vertical translation distance, or lateral translation distance.

According to some embodiments of the present application, the method further comprising:

obtaining the lower limb force line of the surgical object.

According to some embodiments of the present application, the method further comprising:

saving and/or outputting the intraoperative prosthesis planning data.

According to another aspect of the present application, provided is an intraoperative planning adjustment apparatus for TKA, comprising:

an input module configured to import preoperative planning data;

a registration module configured to perform image registration of preoperative planning images with the surface contour of a knee joint of a surgical object;

an acquisition module configured to acquire the motion trajectory information of the knee joint during the continuous flexion-extension of a lower limb;

a calculation module configured to calculate the gap and force line angle of the lower limb at a continuous flexion-extension angle;

an interactive display module configured to visually display the dynamic spacing force line data graph and receive interactive adjustment information; and a storage module configured to save and/or output intraoperative prosthesis planning data.

According to another aspect of the present application, provided is an electronic device for intraoperative planning adjustment of TKA, comprising:

one or more processors; and a storage device configured to store one or more programs, wherein the one or more processors are enabled to implement the foregoing method when the one or more programs are executed by the one or more processors.

According to another aspect, provided is a computer-readable medium, having a computer program stored thereon, and the computer program implements the foregoing method when executed by a processor.

The intraoperative planning adjustment method provided in the present application allows the surgeon to adjust the position of the joint prosthesis and an osteotomy plan by operating the joint prosthesis to conduct up and down, left and right translation, and clockwise and counterclockwise rotation at the reachable flexion-extension angle of the lower limb of the surgical object. In addition, the dynamic spacing force line data graph provides the surgeon with an intuitive and flexible planning basis, and effectively improves the postoperative soft tissue balance.

The additional aspects and advantages of the present application will be set forth in part in the following description and become apparent in part from the following description or be understood through the practice of the present application.

BRIEF DESCRIPTION OF DRAWINGS

In order to more clearly illustrate the technical solution in the embodiments of the present application, the drawings to be used in the description of the embodiments of the present application will be briefly described below. Obviously, the drawings in the following description are some of the embodiments of the present application.

DETAILED DESCRIPTION

The technical solutions in the embodiments of the present application will be described clearly and completely below, and it will be apparent that the embodiments described herein are a part, not all of the embodiments of the present application. All other embodiments obtained by a person of ordinary skill in the art based on the embodiments of the present application without creative efforts shall fall within the protection scope of the present invention.

The terms "first", "second", etc. in the present application are used to distinguish different objects, rather than to describe a specific sequence. In addition, the terms "including" and "having" and any variations thereof are intended to cover non-exclusive inclusion. For example, processes, methods, systems, products, or devices that include a series of steps or units is not limited to the listed steps or units, but optionally include unlisted steps or units, or optionally also include other steps or units inherent in these processes, methods, products or equipment.

Reference to "embodiments" herein means that a specific feature, structure, or characteristic described in conjunction with the embodiments may be included in at least one embodiment of the present application. The appearance of the phrase in various places in the specification does not necessarily refer to the same embodiment, nor is it an independent or alternative embodiment mutually exclusive with other embodiments. Those skilled in the art clearly and implicitly understand that the embodiments described herein can be combined with other embodiments.

In order to solve the problem of single information source and limited adjustment range based on the existing intraoperative planning and adjustment process of TKA, an intraoperative planning and adjustment method for TKA is provided, which allows the surgeon to adjust the position of the joint prosthesis and the osteotomy plan by operating the joint prosthesis to conduct up and down, left and right translation, and clockwise and counterclockwise rotation at the reachable flexion-extension angle of the lower limb of the surgical object. In addition, the dynamic spacing force line data graph provides the surgeon with an intuitive and flexible planning basis, and effectively improves the postoperative soft tissue balance.

The technical solution of the present application will be described in details with reference to accompanying drawings.

Figure 1:
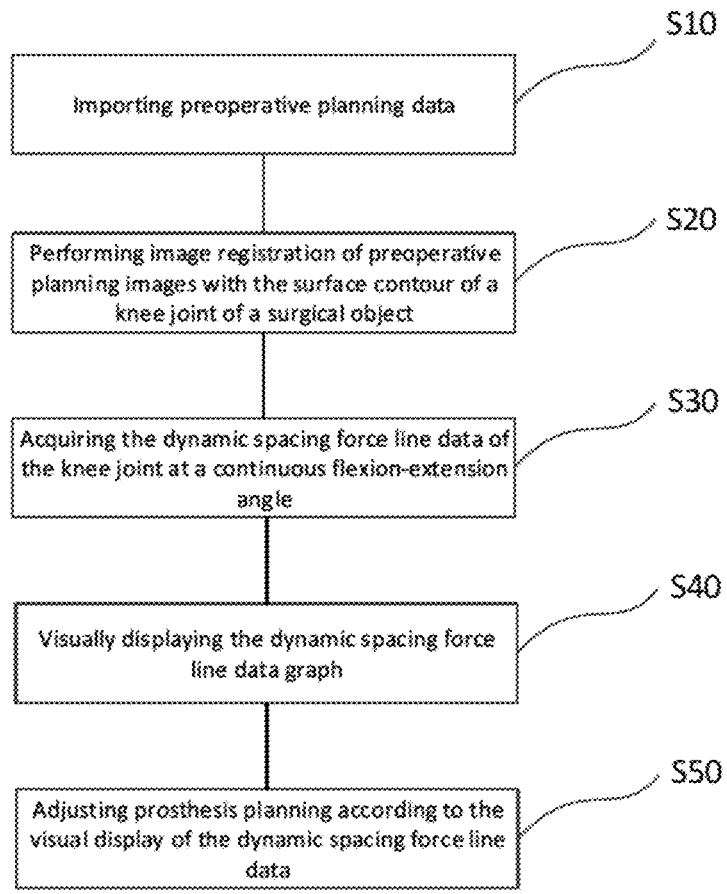
FIG. 1 shows a flowchart of an intraoperative planning adjustment method for TKA according to an exemplary embodiment of the present application.

FIG. 1 shows a flowchart of an intraoperative planning adjustment method for TKA according to an exemplary embodiment of the present application.

As shown in FIG. 1, the intraoperative planning adjustment method for TKA according to an exemplary embodiment of the present application comprises the following steps.

In S10, preoperative planning data is imported. The preoperative planning data includes prosthesis data (such as joint prosthesis model) and a preliminary osteotomy plan formed through preoperative planning. In preoperative planning, a 3D model of the skeletal anatomy of the surgical object is generally generated from the computer tomography (CT) or magnetic resonance imaging (MRI) image data set of the surgical object, the preoperative coordinate system is determined and the image is corrected. A set of 3D models of joint prosthesis is loaded into the system, surgeons are allowed to place the desired joint prosthesis model into the 3D model of the bone anatomy, the position and direction of the joint prosthesis are adjusted to realize the preoperative optimal cooperation of joint prosthesis and bones. Specifically, the prosthesis data includes three-dimensional model data of the joint prosthesis and its corresponding spatial definition in human anatomy. The preliminary osteotomy plan comprises the spatial position and osteotomy plane matching the planned joint prosthesis and generated by the three-dimensional planning of the joint prosthesis and the patient's bone model.

In S20, image registration is performed between the preoperative planning image and the surface contour of the knee joint of the surgical object. The purpose of registration is to establish a match between the virtual 3D model and the real bones. The specific registration method can be to use a structured light navigator to take multiple points on the surface of the bone with a probe, and to calculate the center of the femoral head by rotating the femur. This solution uses a point cloud registration algorithm to achieve precise registration of the joint surfaces of the femur and tibia respectively. For example, a rough registration of six marking points can be performed first, then a fine registration of multiple points, and finally the registration result can be verified.

In S30, the dynamic-interval force line data of the knee joint at a continuous flexion-extension angle is obtained. According to an exemplary embodiment of the present application, the acquiring the dynamic spacing force line data of the knee joint at a continuous flexion-extension angle comprises acquiring the motion trajectory information of the knee joint during the continuous flexion-extension of the lower limb; and calculating the gap and the force line angle at the continuous flexion-extension angle of the lower limb.

Specifically, for example, the acquisition of the movement trajectory information of the knee joint during the continuous flexion-extension of the lower limb comprises setting tracers on the femur and tibia of the knee joint; and during the continuous flexion-extension of the lower limb, continuously tracking the tracers by an optical camera, and acquiring and recording the motion trajectory information of the knee joint.

According to an exemplary embodiment of the present application, the gap includes a first gap and a second gap. The first gap is the minimum gap between the outer surface of the medial femoral condyle of the prosthesis and the tibial osteotomy plane. The second gap is the minimum gap between the outer surface of the lateral femoral condyle of the prosthesis and the tibial osteotomy plane. The force line angle is the angle between the femoral mechanical axis and the tibial mechanical axis.

In S40, the dynamic spacing force line data graph is displayed visually. The dynamic spacing force line data graph includes a first gap graph, a second gap graph, and a force line angle change graph. The first gap graph is drawn by taking the flexion-extension angle of the lower limb as the ordinate and the first gap as the abscissa. The second gap graph is drawn by taking the flexion-extension angle of the lower limb as the ordinate and the second gap as the abscissa. The force line angle change graph is drawn by taking the flexion-extension angle of the lower limb as the ordinate and the force line angle as the abscissa.

According to some embodiments of the present application, the recorded gap and force line data of the lower limb at a certain reachable flexion-extension angle can be stored as a one-time spacing force line data graph, and can be recorded and stored multiple times.

According to some other embodiments of the present application, it is also possible to record the gaps and force line data at a plurality of reachable flexion-extension angles, and draw the multiple gaps and force line data as a continuous curve, and store the continuous curve as a spacing force line data graph. Similarly, the multiple gaps and force line data can also be recorded and stored multiple times.

In S50, the prosthesis planning is adjusted according to the visual display of the dynamic spacing force line data. In the visual display, interactively editable prosthesis position information is provided, including varus/valgus angle, external/internal rotation angle, anterior/posterior slope angle, vertical translation distance, and lateral translation distance. The surgeon can interactively adjust the position of the prosthesis through a visual display interface. According to the received position adjustment information of the prosthesis, the gap and force line will be recalculated and the dynamic spacing force line data graph will be refreshed.

The visual display provides the surgeon with an intuitive and clear planning adjustment result. The surgeon can continuously adjust the prosthesis position information according to the visual display of the dynamic spacing force line data graph until the content displayed by the dynamic spacing force line data graph reaches the requirement of the surgeon.

In the foregoing method, accurately calculating the gap and force line angle of the lower limb at a continuous flexion-extension angle is the key of the method. The detailed description will be given below with reference to FIGS. 2 to 4.

Figure 2:
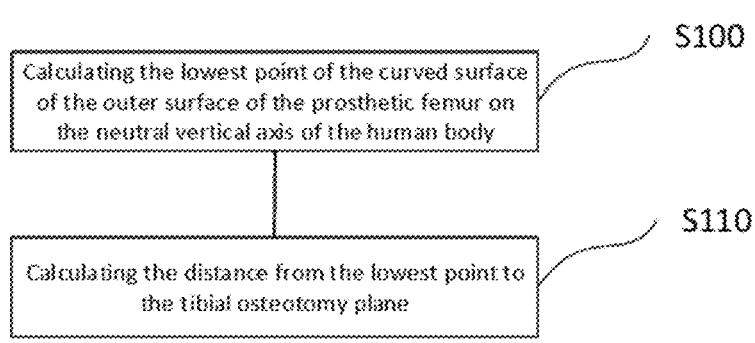
FIG. 2 shows a flowchart of gap calculation according to an exemplary embodiment of the present application.

FIG. 2 shows a flowchart of gap calculation according to an exemplary embodiment of the present application.

As shown in FIG. 2, according to an exemplary embodiment of the present application, a method for calculating the gap comprises the following steps.

In S100, the lowest point of the curved surface of the outer surface of the prosthetic femur on the neutral vertical axis of the human body. During the calculating of the first gap, the outer surface of the prosthetic femoral medial condyle is used. During the calculating of the first gap, the outer surface of the prosthetic femoral lateral condyle is used.

In S110, the distance from the lowest point to the tibial osteotomy plane is calculated. The calculated distance is the distance from a three-dimensional space surface to another three-dimensional space plane, which can more truly reflect the motion state of the knee joint.

Figure 3:
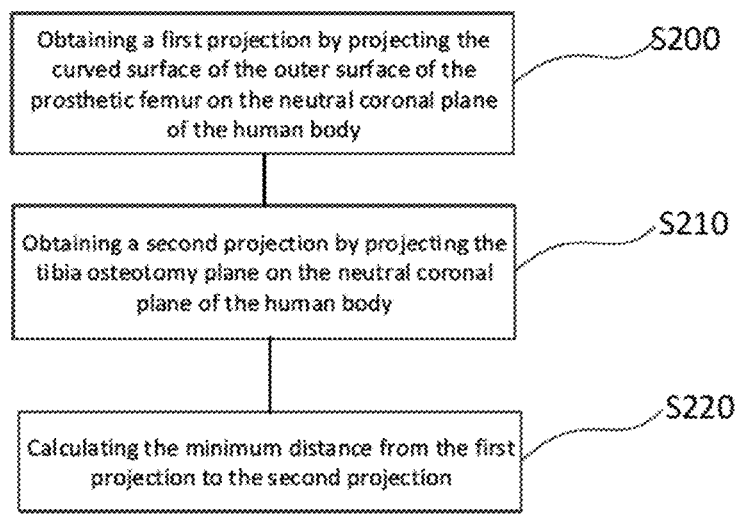
FIG. 3 shows a flowchart of gap calculation according to another exemplary embodiment of the present application.

FIG. 3 shows a flowchart of gap calculation according to another exemplary embodiment of the present application.

As shown in FIG. 3, according to another exemplary embodiment of the present application, another method for calculating the gap comprises the following steps.

In S200, a first projection is obtained by projecting the curved surface of the outer surface of the prosthetic femur on the neutral coronal plane of the human body. During the calculating of the first gap, the outer surface of the prosthetic femoral medial condyle is used. During the calculating of the first gap, the outer surface of the prosthetic femoral lateral condyle is used.

In S210, a second projection is obtained by projecting the tibia osteotomy plane on the neutral coronal plane of the human body.

In S230, the minimum distance from the first projection to the second projection is calculated. The calculated gap is the distance from a two-dimensional plane to another two-dimensional plane.

Figure 4:
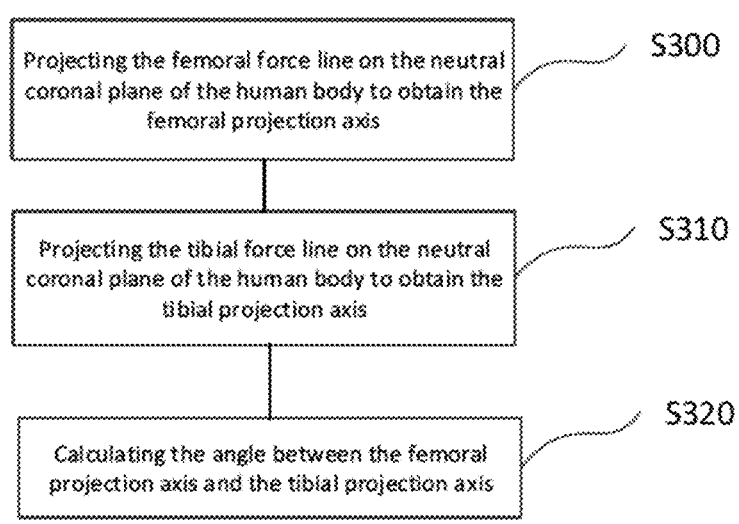
FIG. 4 shows a flowchart of calculating a force line angle according to an exemplary embodiment of the present application.

FIG. 4 shows a flowchart of calculating a force line angle according to an exemplary embodiment of the present application.

As shown in FIG. 4, a method for calculating the force line angle comprises the following steps.

In S300, the femoral mechanical axis is projected on the neutral coronal plane of the human body to obtain the femoral projection axis.

In S310, the tibial mechanical axis is projected on the neutral coronal plane of the human body to obtain the tibial projection axis.

In S320, the angle between the femoral projection axis and the tibial projection axis is calculated.

Figure 5:
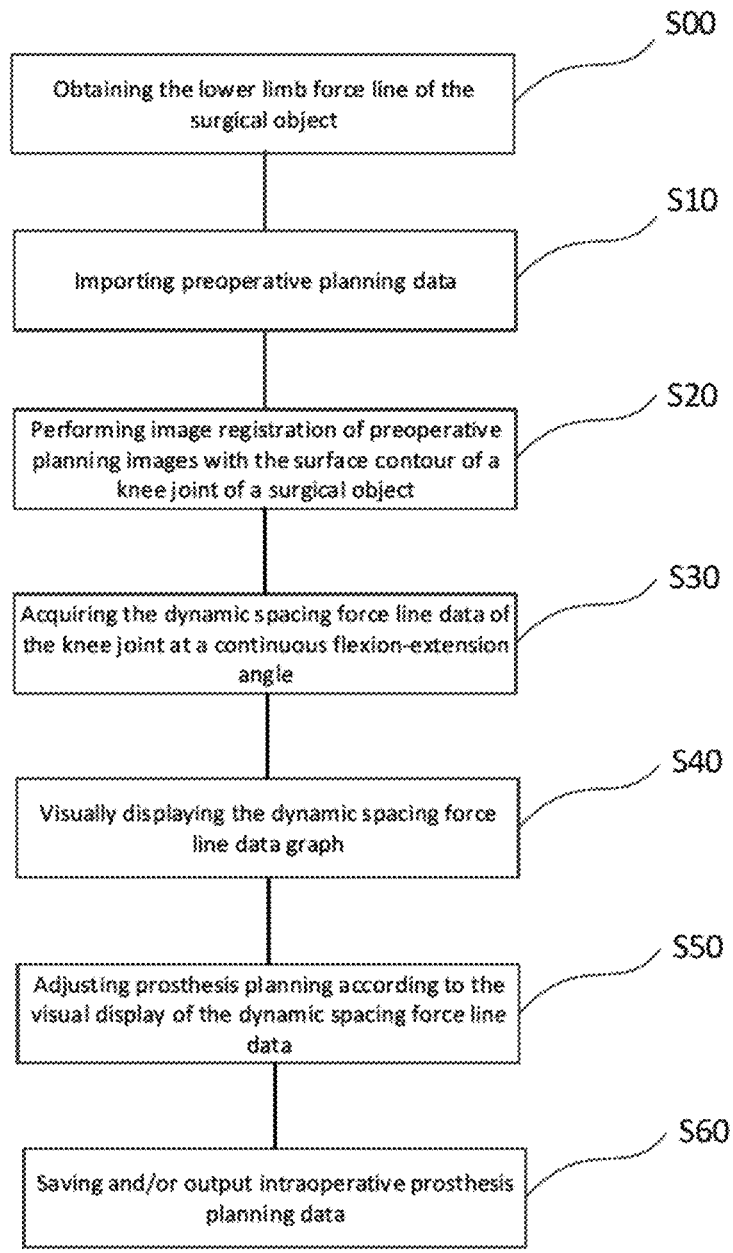
FIG. 5 shows a flowchart of an intraoperative planning adjustment method for TKA according to another exemplary embodiment of the present application.

FIG. 5 shows a flowchart of an intraoperative planning adjustment method for TKA according to another exemplary embodiment of the present application.

As shown in FIG. 5, the intraoperative planning adjustment method for TKA according to another exemplary embodiment of the present application further comprises the following steps.

In S00, the lower limb force line of the surgical object is obtained. The actual lower limb force line of the surgical object is an important reference standard for the surgeon in the planning adjustment process. To obtain the true force line during the operation, by obtaining the center of the femoral head and marking the bony markers, the center of the femoral condyle, the center of the tibial plateau, and the center of the ankle point can be determined, so as to obtain the true lower limb force line.

In S60, the intraoperative prosthesis planning data is saved and/or output. The adjusted prosthesis planning data can be saved locally or output to an actuator.

The intraoperative planning adjustment method provided in the present application can be iteratively performed many times. For example, the first intraoperative planning adjustment is made through the first recorded lower limb movement trajectory information, the planning results are output to the actuator, and the actuator performs the first osteotomy. After that, the lower limb movement trajectory information is recorded for the second time, and the second intraoperative planning adjustment and the second osteotomy are performed. The same operation is performed on and on, until the osteotomy effect satisfactory to the surgeon is achieved.

Figure 6:
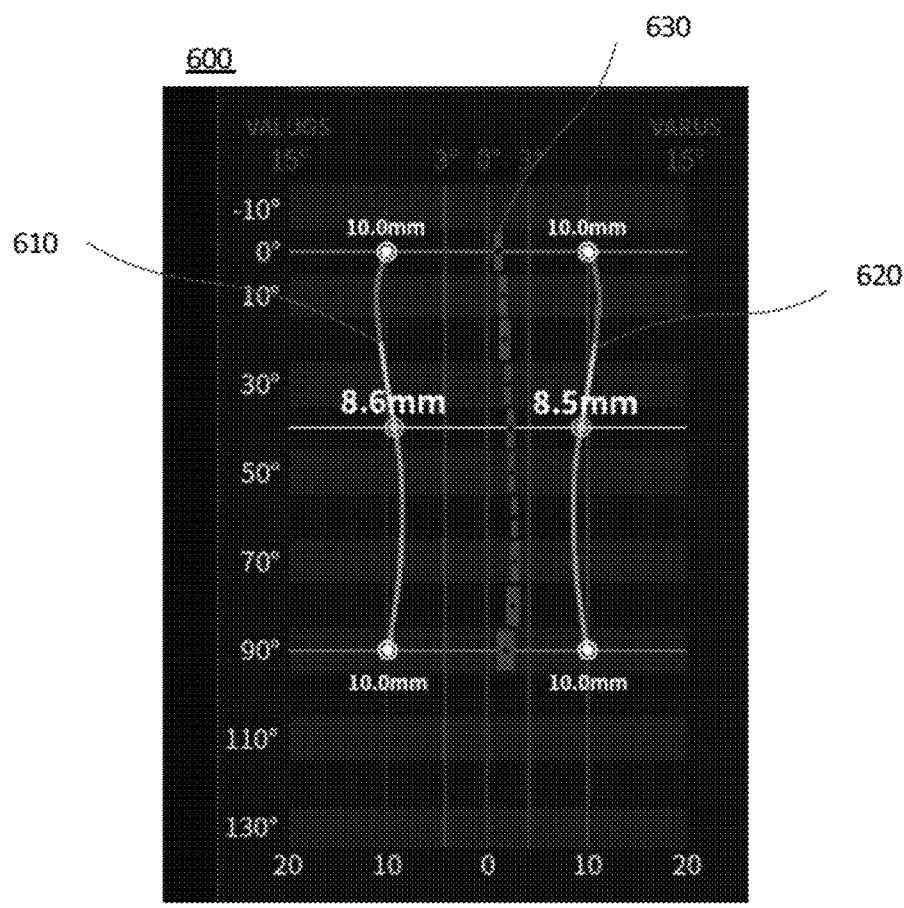
FIG. 6 shows a photo of a dynamic spacing force line data graph according to an exemplary embodiment of the present application.

FIG. 6 shows a photo of a dynamic spacing force line data graph according to an exemplary embodiment of the present application.

As shown in FIG. 6, the visual dynamic spacing force line data graph 600 provided according to the present application includes: a first gap curve 610, a second gap curve 620, and a force line angle change curve 630. The ordinates of the first gap curve 610, the second gap curve 620, and the force line angle change curve 630 are all lower limb flexion-extension angles. The reachable flexion-extension angle of the human knee joint ranges from −10° to 130°.

Referring to FIG. 6, the first gap curve 610 takes the first gap as the first abscissa, and the second gap curve 620 takes the second gap as the second abscissa. The first abscissa and the second abscissa share an origin to form a gap abscissa. The gap abscissa may be set below the dynamic spacing force line data graph, and extend positively to the left and right sides, and the first gap curve and the second gap curve are respectively set on both sides of the origin of the gap abscissa.

As shown in FIG. 6, the force line angle change curve 630 takes the force line angle as the abscissa. The force line angle abscissa can be set at the top part of the dynamic spacing force line data graph. The origin is in the middle position, one side of the origin is positive and the other side is negative. The force line angle is controlled between −3° and 3°, and the postoperative soft tissue can achieve a better balance.

Figure 7:
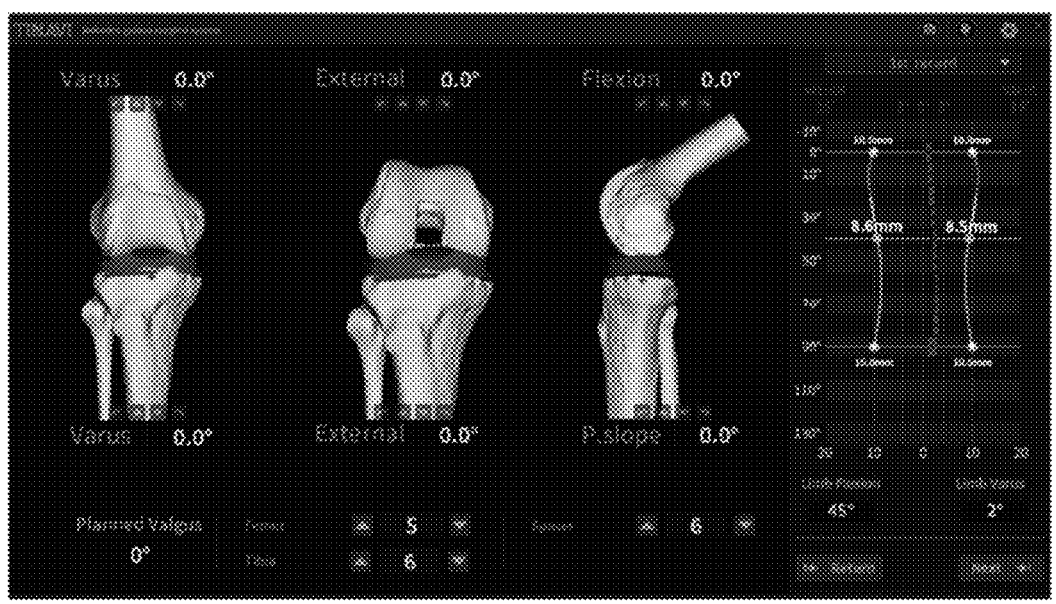
FIG. 7 shows a photo 1 of the interactive interface of the intraoperative planning adjustment method for TKA according to an exemplary embodiment of the present application.

FIG. 7 shows a first photo of the interactive interface of the intraoperative planning adjustment method for TKA according to an exemplary embodiment of the present application.

As shown in FIG. 7, the interactive interface includes a left part and a right part. The view of the left part includes three knee joint views, which respectively represent the knee joint and prosthesis state when the flexion-extension angles are 0°, 45°, and 90°. In addition, the left part also provides editable prosthesis data parameters for the surgeon to adjust the planning. Specifically, the parameters include:

Varus/valgus angle: the varus/valgus angle (Vaus/Valgus) between the femur/tibia prosthesis and bone. When the prosthesis is varus relative to the bone, the degree of the Varus angle is displayed. If the angle is 0°, it is displayed as Varus/Valgus 0°. When the prosthesis is valgus relative to the bone, the degree of the Valgus angle is displayed.

Internal/external rotation angle: the internal/external rotation angle (External/Internal) of the femur/tibia prosthesis relative to the bone. When the prosthesis is externally rotated relative to the bone, the degree of external rotation (External) is displayed. If the degree of external rotation is 0, it is displayed as External/Internal 0°. When the prosthesis is internally rotated relative to the bone, the degree of internal rotation (Internal) is displayed.

Planned Varus/Valgus: The planned force line angle of the lower limb at the currently selected flexion-extension angle.

The right part mainly includes the dynamic spacing force line data graph as shown in FIG. 6, which will not be repeated here.

Figure 8:
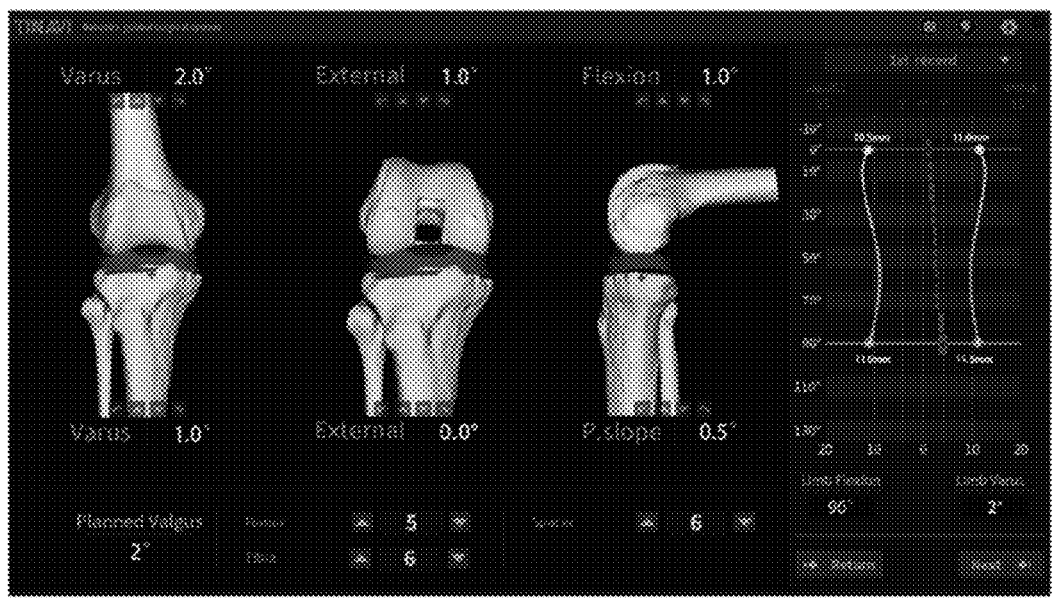
FIG. 8 shows a photo 2 of the interactive interface of the intraoperative planning adjustment method for TKA according to an exemplary embodiment of the present application.

FIG. 8 shows a second photo of the interactive interface of the intraoperative planning adjustment method for TKA according to an exemplary embodiment of the present application.

The intraoperative planning adjustment method for TKA provided in the present application not only provides visual data display for the surgeon, but also provides the surgeon with interactive planning adjustment.

When the surgeon adjusts the prosthesis parameter information in the left part of FIG. 8, such as adjusting the varus angle, internal and external rotation angle, etc., after the interactive interface receives the adjusted prosthesis parameter information, the first gap, the second gap, and the force line angle are recalculated by the methods shown in FIGS. 2 to 4, and the adjusted dynamic spacing force line data graph is displayed on the right side of the interactive interface in real time. As shown in FIG. 8, it is the interactive interface after the prosthesis parameters are adjusted.

Figure 9:
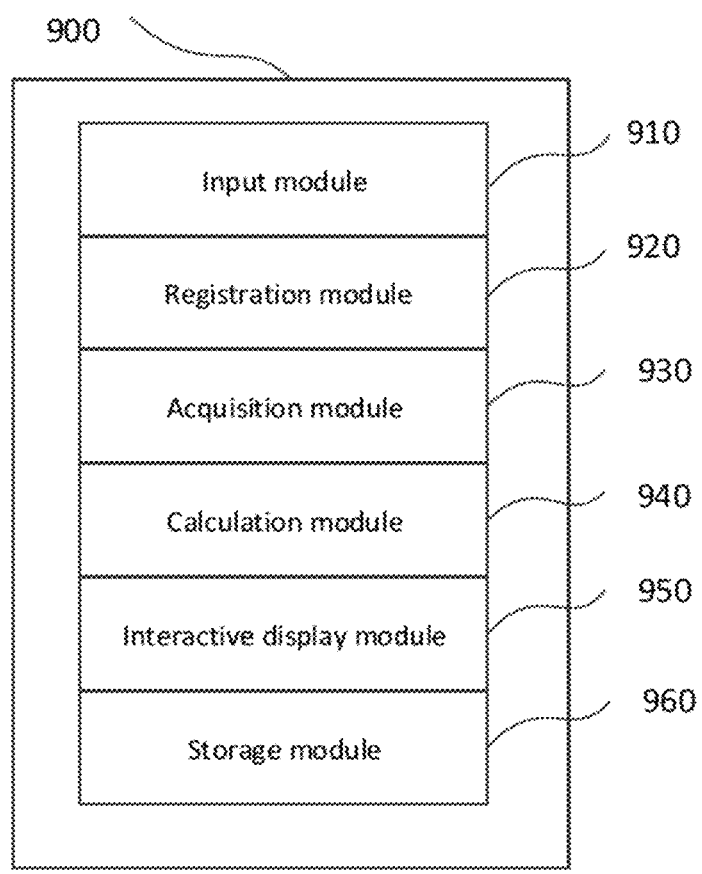
FIG. 9 shows a block diagram of an intraoperative planning adjustment device for TKA according to an exemplary embodiment of the present application.

FIG. 9 shows a block diagram of an intraoperative planning adjustment device for TKA according to an exemplary embodiment of the present application.

As shown in FIG. 9, according to another aspect of the present application, provided is an intraoperative planning adjustment apparatus 900 for TKA, comprising an input module 910, a registration module 920, an acquisition module 930, a calculation module 940, an interactive display module 950, and a storage module 960, wherein:

the input module 910 is configured to import preoperative planning data;

the registration module 920 is configured to perform registration of preoperative planning images with the surface contour of a knee joint of a surgical object;

the acquisition module 930 is configured to acquire the motion trajectory information of the knee joint during the continuous flexion-extension of a lower limb;

the calculation module 940 is configured to calculate the gap and force line angle of the lower limb at a continuous flexion-extension angle;

the interactive display module 950 is configured to visually display the dynamic spacing force line data graph and receive interactive adjustment information; and the storage module 960 is configure to save and/output intraoperative planning adjustment data.

Figure 10:
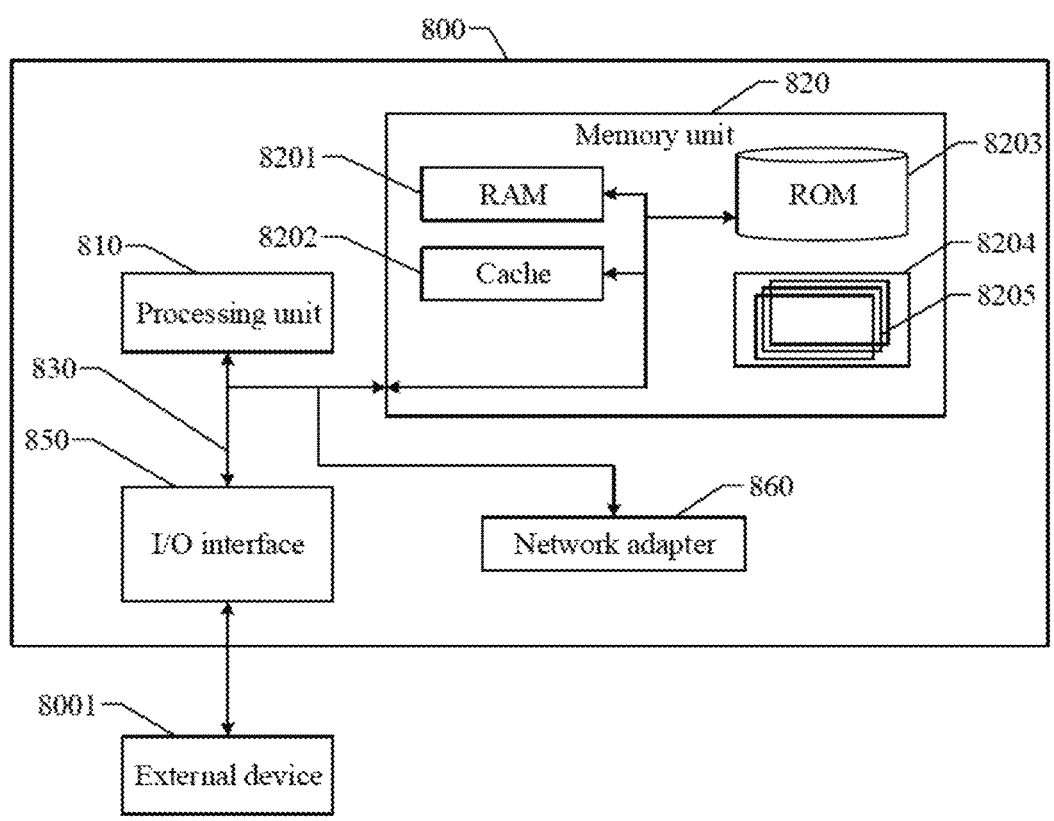
FIG. 10 shows a block diagram of an electronic device according to an exemplary embodiment of the present application.

FIG. 10 shows a block diagram of an electronic device according to an exemplary embodiment of the present application.

The electronic device 800 according to this embodiment of the present application will be described below with reference to FIG. 10. The electronic device 800 shown in FIG. 8 is only an example, and in no way limits the function and scope of use of the embodiments of the present application.

As shown in FIG. 8, the electronic device 800 is represented in the form of a general-purpose computing device. The components of the computer system/server 800 may include but are not limited to: at least one processing unit 810, at least one storage unit 820, and a bus 830 connecting different system components (including the storage unit 820 and the processing unit 810).

The storage unit 820 stores program codes which can be executed by the processing unit 810, so that the processing unit 810 executes the methods described in the present specification according to the embodiments of the present application.

The storage unit 820 may include a readable medium in the form of a volatile storage unit, such as a random access storage unit (RAM) 8201 and/or a cache storage unit 8202, and may further include a read-only storage unit (ROM) 8203.

The storage unit 820 may also include a program/utility tool 8204 having a set of (at least one) program module 8205. Such program module 8205 includes but is not limited to: an operating system, one or more application programs, other program modules, and program data, Each of these examples or some combinations thereof may include the implementation of a network environment.

The bus 830 may represent one or more of several types of bus structures, including a storage bus or a memory controller, a peripheral bus, a graphic acceleration port, a processing unit, or a local bus using any of a variety of bus architectures.

The electronic device 800 may also communicate with one or more external devices 8001 (such as touch screens, keyboards, pointing devices, and Bluetooth devices), and may also communicate with one or more devices that enable a user to interact with the electronic device 800, and/or communicate with any device (such as a router and a modem) that enables the electronic device 800 to communicate with one or more other computing devices. This communication can be made via an input/output (I/O) interface 850. Moreover, the electronic device 800 may also communicate with one or more networks (e.g., a local area network (LAN), a wide area network (WAN), and/or a public network, such as the Internet) via a network adapter 860. The network adapter 860 may communicate with other modules of the electronic device 800 via the bus 830. It should be appreciated that although not shown in the figure, other hardware and/or software modules, including, but not limited to, microcode, device drivers, redundant processing units, external magnetic disk drive arrays. RAID systems, tape drives, and data backup storage systems, etc., may be used in conjunction with the electronic device 800.

The present application further provides a computer-readable medium, having a computer program stored thereon, and the program implements the steps of the foregoing method when executed by a processor.

The intraoperative planning adjustment method provided in the present application allows the surgeon to adjust the position of the joint prosthesis and an osteotomy plan by operating the joint prosthesis to conduct up and down, left and right translation, and clockwise and counterclockwise rotation at the reachable flexion-extension angle of the lower limb of the surgical object. In addition, the dynamic spacing force line data graph provides the surgeon with an intuitive and flexible planning basis, and effectively improves the postoperative soft tissue balance.

It should be noted that the above-described embodiments are examples merely illustrative of the present invention and are not intended to limit the implementations. Other variations or modifications of the various forms may be made by those skilled in the art in light of the above description. There is no need and no way to exhaust all of the implementations. Obvious changes or variations resulting therefrom are still within the scope of the present application.

The invention claimed is:

1. An intraoperative planning adjustment method for Total Knee Arthroplasty (TKA) via a computer-aided system, comprising:
    importing, by the computer-aided system, preoperative planning data;
    performing, by the computer-aided system, image registration of preoperative planning images with the surface contour of a knee joint of a surgical subject;
    acquiring, by the computer-aided system, the dynamic spacing force line data of the knee joint at a continuous flexion-extension angle, comprising:
        setting a plurality of tracers on the femur and tibia of the knee joint;
        acquiring, by the computer-aided system, the motion trajectory information of the knee joint during the continuous flexion-extension of a lower limb by continuously tracking the plurality of tracers via an optical camera;
        calculating, by the computer-aided system, the gap and force line angle of the lower limb at a continuous flexion-extension angle;
        wherein the gap and force line angle comprise:
            a first gap, being a minimum gap between the outer surface of the medial femoral condyle of the prosthesis and the tibial osteotomy plane;
            a second gap, being a minimum gap between the outer surface of the lateral femoral condyle of the prosthesis and the tibial osteotomy plane; and
            a force line angle, being an angle between a femoral mechanical axis and a tibial mechanical axis;
    visually displaying, by the computer-aided system, the dynamic spacing force line data as a graph; wherein the graph for the dynamic spacing force line data comprises:
        a first gap curve, a continuous curve drawn by taking the flexion-extension angle of the lower limb as an ordinate and the first gap as a first abscissa;
        a second gap curve, a continuous curve drawn by taking the flexion-extension angle of the lower limb as an ordinate and the second gap as a first abscissa; and
        a force line angle change curve, drawn by taking the flexion-extension angle of the lower limb as an ordinate and the force line angle as an abscissa;
    adjusting, by the computer-aided system, prosthesis planning according to the visual display of the dynamic spacing force line data.

2. The adjustment method according to claim 1, wherein the preoperative planning data comprises joint prosthesis data and/or a preliminary osteotomy plan.

3. The adjustment method according to claim 1, wherein calculating the gap comprises:
    calculating, by the computer-aided system, the lowest point of the curved surface of the outer surface of the prosthetic femur on the neutral vertical axis of the human body; and
    calculating, by the computer-aided system, the distance from the lowest point to the tibial osteotomy plane.

4. The adjustment method according to claim 1, wherein calculating the gap comprises:
    obtaining, by the computer-aided system, a first projection by projecting the curved surface of the outer surface of the prosthetic femur on the neutral coronal plane of the human body;
    obtaining, by the computer-aided system, a second projection by projecting the tibia osteotomy plane on the neutral coronal plane of the human body; and
    calculating, by the computer-aided system, the minimum distance from the first projection to the second projection.

5. The adjustment method according to claim 1, wherein calculating the force line angle comprises:
    projecting, by the computer-aided system, the femoral mechanical axis on the neutral coronal plane of the human body to obtain a femoral projection axis;
    projecting, by the computer-aided system, the tibial force line on the neutral coronal plane of the human body to obtain the tibial projection axis; and
    calculating, by the computer-aided system, the angle between the femoral projection axis and the tibial projection axis.

6. The adjustment method according to claim 1, wherein the midpoint of the first abscissa is the origin and extends positively to the left and right sides, and the first gap curve and the second gap curve are respectively arranged on both sides of the midpoint of the first abscissa.

7. The adjustment method according to claim 1, wherein the adjusting prosthesis planning comprises:
    receiving, by the computer-aided system, position adjustment information of the prosthesis interacted by the surgeon; and recalculating the gap and force line and refreshing the graph for the dynamic spacing force line data.

8. The adjustment method according to claim 7, wherein the prosthesis position information comprises at least one of varus/valgus angle, external/internal rotation angle, anterior/posterior slope angle, vertical translation distance, or lateral translation distance.

9. The adjustment method according to claim 1, further comprising: obtaining, by the computer-aided system, the lower limb force line of the surgical subject.

10. The adjustment method according to claim 1, further comprising: saving and/or outputting, by the computer-aided system, the intraoperative prosthesis planning data.

11. An electronic device for intraoperative planning adjustment of Total Knee Arthroplasty (TKA) via a computer-aided system, comprising:
    one or more processors; and a storage device configured to store one or more programs, wherein the one or more processors are enabled to implement the method according to claim 1 when the one or more programs are executed by the one or more processors.

12. A non-transitory computer-readable medium, having a computer program stored thereon, wherein the computer program implements an intraoperative planning adjustment method for Total Knee Arthroplasty (TKA) via a computer-aided system when executed by a processor:

the method comprising:
importing, by the computer-aided system, preoperative planning data;
performing, by the computer-aided system, image registration of preoperative planning images with the surface contour of a knee joint of a surgical subject;
acquiring, by the computer-aided system, the dynamic spacing force line data of the knee joint at a continuous flexion-extension angle, comprising:
  setting a plurality of tracers on the femur and tibia of the knee joint;
  acquiring, by the computer-aided system, the motion trajectory information of the knee joint during the continuous flexion-extension of a lower limb by continuously tracking the plurality of tracers via an optical camera;
  calculating, by the computer-aided system, the gap and force line angle of the lower limb at a continuous flexion-extension angle;
wherein the gap and force line angle comprises:
  a first gap, being a minimum gap between the outer surface of the medial femoral condyle of the prosthesis and the tibial osteotomy plane;
  a second gap, being a minimum gap between the outer surface of the lateral femoral condyle of the prosthesis and the tibial osteotomy plane; and
  a force line angle, being an angle between a femoral mechanical axis and a tibial mechanical axis;
visually displaying, by the computer-aided system, the dynamic spacing force line data as a graph; wherein the graph for the dynamic spacing force line data comprises:
a first gap curve, a continuous curve drawn by taking the flexion-extension angle of the lower limb as an ordinate and the first gap as a first abscissa;
a second gap curve, a continuous curve drawn by taking the flexion-extension angle of the lower limb as an ordinate and the second gap as a first abscissa; and
a force line angle change curve, drawn by taking the flexion-extension angle of the lower limb as an ordinate and the force line angle as an abscissa;
adjusting, by the computer-aided system, prosthesis planning according to the visual display of the dynamic spacing force line data.

13. The non-transitory computer-readable medium according to claim 12, wherein the preoperative planning data comprises joint prosthesis data and/or a preliminary osteotomy plan.

* * * * *